US012749257B2

(12) United States Patent
Breivik

(10) Patent No.: US 12,749,257 B2
(45) Date of Patent: Sep. 29, 2026

(54) SYSTEM FOR DYNAMICALLY REMOVING ANATOMICAL STRUCTURES FROM A VOLUME-RENDERED IMAGE BASED ON A POSITION OF A VIRTUAL LIGHT SOURCE

(71) Applicant: GE Precision Healthcare LLC, Waukesha, WI (US)

(72) Inventor: Lars Hofsøy Breivik, Oslo (NO)

(73) Assignee: GE Precision Healthcare LLC, Waukesha, WI (US)

( * ) Notice: Subject to any disclaimer, the term of this patent is extended or adjusted under 35 U.S.C. 154(b) by 134 days.

(21) Appl. No.: 18/933,191

(22) Filed: Oct. 31, 2024

(65) Prior Publication Data

US 2026/0120387 A1 Apr. 30, 2026

(51) Int. Cl.

| | |
|---|---|
| ***G06T 15/08*** | (2011.01) |
| ***A61B 6/46*** | (2024.01) |
| ***A61B 8/00*** | (2006.01) |
| ***G06T 15/50*** | (2011.01) |

(52) U.S. Cl.
CPC ............ *G06T 15/08* (2013.01); *G06T 15/506* (2013.01); *A61B 6/466* (2013.01); *A61B 8/466* (2013.01); *G06T 2200/04* (2013.01); *G06T 2200/24* (2013.01); *G06T 2210/41* (2013.01)

(58) Field of Classification Search
None
See application file for complete search history.

(56) References Cited

U.S. PATENT DOCUMENTS

| | | | | |
|---|---|---|---|---|
| 10,896,538 | B2 | 1/2021 | Mory et al. | |
| 11,367,237 | B2 | 6/2022 | Breivik | |
| 11,619,737 | B2 | 4/2023 | Breivik | |
| 2016/0292913 | A1* | 10/2016 | Wahrenberg | A61B 6/466 |
| 2017/0020485 | A1 | 1/2017 | Kim et al. | |
| 2019/0147645 | A1 | 5/2019 | Mory et al. | |
| 2021/0174476 | A1 | 6/2021 | Hvidsten Blytt | |
| 2022/0254094 | A1* | 8/2022 | Wahrenberg | G06T 7/70 |

* cited by examiner

*Primary Examiner* — Michael J Cobb
(74) *Attorney, Agent, or Firm* — SPQ IP LLC

(57) ABSTRACT

A system may receive three-dimensional (3D) medical imaging data of a region of interest of a subject. The system may generate a first volume-rendered image of anatomical structures of the region of interest of the subject, and display the first volume-rendered image. The system may receive a user input that selects a position of a virtual light source relative to the anatomical structures in the first volume-rendered image. The system may determine respective irradiation parameters of the anatomical structures based on the position of the virtual light source relative to the anatomical structures of the region of interest. The system may generate a second volume-rendered image by removing one or more anatomical structures, of the anatomical structures, from the first volume-rendered image based on the respective irradiation parameters of the anatomical structures. The system may simultaneously display the first volume-rendered image and the second volume-rendered image.

20 Claims, 11 Drawing Sheets

SYSTEM FOR DYNAMICALLY REMOVING ANATOMICAL STRUCTURES FROM A VOLUME-RENDERED IMAGE BASED ON A POSITION OF A VIRTUAL LIGHT SOURCE

TECHNICAL FIELD

The present disclosure relates to a system for displaying volume-rendered images. More specifically, the present disclosure relates to a system for receiving a user input that selects a position of a virtual light source relative to anatomical structures of a region of interest of a subject in a first volume-rendered image, and dynamically generates a second volume-rendered image by removing one or more anatomical structures, of the anatomical structures, from the first volume-rendered image based on respective irradiation parameters of the anatomical structures.

BACKGROUND

A volume-rendered image may be a two-dimensional (2D) representation of three-dimensional (3D) medical imaging data of a region of interest of a subject. The region of interest of the subject may include various anatomical structures. A system may generate a volume-rendered image using the 3D medical imaging data and a volume-rendering technique, such as ray tracing, ray casting, photon mapping, scanline rendering, or the like. The volume-rendered image may include optical effects, such as reflection, refraction, shadowing, depth of field, ambient occlusion, or the like. Further, the system may permit a virtual light source to be positioned relative to an anatomical structure to irradiate the anatomical structure. In this way, the volume-rendered image may enable a clinician to assess the shape, structure, and position of an anatomical structure displayed in the volume-rendered image.

A region of interest of a subject may include various anatomical structures. A clinician might be interested in viewing a particular anatomical structure for assessment. However, in some cases, the anatomical structure might be partially, or entirely, obfuscated or occluded by anatomical structures that are not of interest to the subject or are of limited interest to the subject. In these cases, the clinician might find it difficult to assess the particular anatomical structure. Accordingly, the volume-rendered image might be of low quality for examination purposes, might be unusable for examination purposes, might be inaccurate for examination purposes, or the like. In this way, the displayed volume-rendered images might not permit an accurate assessment by a clinician of the region of interest, which might inhibit subject safety, or the like.

SUMMARY

This summary introduces concepts that are described in more detail in the detailed description. It should not be used to identify essential features of the claimed subject matter, nor to limit the scope of the claimed subject matter.

In an aspect, a system may include a memory configured to store instructions; and one or more processors configured to execute the instructions to: receive three-dimensional (3D) medical imaging data of a region of interest of a subject; generate a first volume-rendered image of anatomical structures of the region of interest of the subject; display the first volume-rendered image of anatomical structures of the region of interest of the subject; receive a user input that selects a position of a virtual light source relative to the anatomical structures of the region of interest of the subject in the first volume-rendered image; determine respective irradiation parameters of the anatomical structures of the region of interest of the subject based on the position of the virtual light source relative to the anatomical structures of the region of interest; generate a second volume-rendered image by removing one or more anatomical structures, of the anatomical structures, from the first volume-rendered image based on the respective irradiation parameters of the anatomical structures; and simultaneously display the first volume-rendered image and the second volume-rendered image.

In another aspect, a method may include receiving three-dimensional (3D) medical imaging data of a region of interest of a subject; generating a first volume-rendered image of anatomical structures of the region of interest of the subject; displaying the first volume-rendered image of anatomical structures of the region of interest of the subject; receiving a user input that selects a position of a virtual light source relative to the anatomical structures of the region of interest of the subject in the first volume-rendered image; determining respective irradiation parameters of the anatomical structures of the region of interest of the subject based on the position of the virtual light source relative to the anatomical structures of the region of interest; generating a second volume-rendered image by removing one or more anatomical structures, of the anatomical structures, from the first volume-rendered image based on the respective irradiation parameters of the anatomical structures; and simultaneously displaying the first volume-rendered image and the second volume-rendered image.

In yet another aspect, a non-transitory computer-readable medium may store instructions that, when executed by one or more processors, cause the one or more processors to receive three-dimensional (3D) medical imaging data of a region of interest of a subject; generate a first volume-rendered image of anatomical structures of the region of interest of the subject; display the first volume-rendered image of anatomical structures of the region of interest of the subject; receive a user input that selects a position of a virtual light source relative to the anatomical structures of the region of interest of the subject in the first volume-rendered image; determine respective irradiation parameters of the anatomical structures of the region of interest of the subject based on the position of the virtual light source relative to the anatomical structures of the region of interest; generate a second volume-rendered image by removing one or more anatomical structures, of the anatomical structures, from the first volume-rendered image based on the respective irradiation parameters of the anatomical structures; and simultaneously display the first volume-rendered image and the second volume-rendered image.

DETAILED DESCRIPTION

Figure 1:
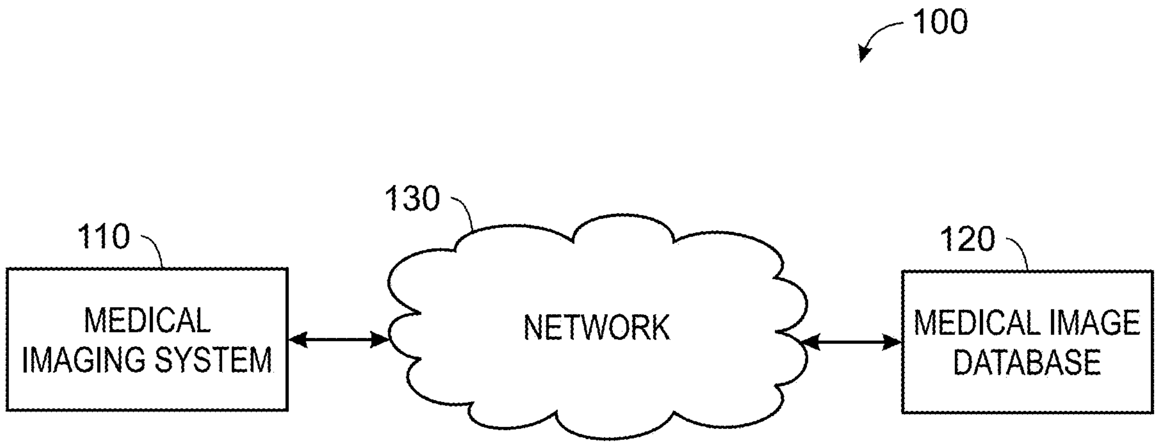
FIG. 1 is a diagram of an example system for dynamically removing anatomical structures from a volume-rendered image based on a position of a virtual light source.

As addressed above, a volume-rendered image of a region of interest of a subject may include various anatomical structures that are of varying importance for assessment by a clinician. For instance, anatomical structures of low importance might partially, or entirely, obfuscate or occlude anatomical structures of significant importance for assessment. The clinician might not be able to accurately assess the region of interest based on this obfuscation or occlusion. In such cases, the diagnostic assessment might be partially, or entirely, inhibited, which may inhibit subject safety. Further, the clinician might be required to spend an inordinate amount of time manipulating or reviewing the volume-rendered image to attempt to assess the region of interest.

Some embodiments herein provide a system for dynamically removing anatomical structures from a volume-rendered image based on a position of a virtual light source. For instance, some embodiments herein provide a system that receives 3D medical imaging data of a region of interest of a subject, generates a first volume-rendered image of anatomical structures of the region of interest of the subject, displays the first volume-rendered image of anatomical structures of the region of interest of the subject, receives a user input that selects a position of a virtual light source relative to the anatomical structures of the region of interest of the subject in the first volume-rendered image, determines respective irradiation parameters of the anatomical structures of the region of interest of the subject based on the position of the virtual light source relative to the anatomical structures of the region of interest, generates a second volume-rendered image by removing one or more anatomical structures, of the anatomical structures, from the first volume-rendered image based on the respective irradiation parameters of the anatomical structures, and simultaneously displays the first volume-rendered image and the second volume-rendered image.

Accordingly, the system may remove anatomical structures that are partially, or entirely, occluding or obfuscating anatomical structures of interest. In this way, the system generates volume-rendered images that allow a clinician to more accurately, comprehensively, and/or quickly assess a region of interest, which improves the assessment of the region of interest and/or improves subject safety by permitting more accurate or comprehensive diagnosis. Further, the system may simultaneously display the first volume-rendered image and the second volume-rendered image, which permits the user to manipulate the position of the virtual light source in the first volume-rendered image and permits the second volume-rendered image to be updated accordingly.

In this way, some embodiments herein provide a technical improvement in the technical field of medical imaging by generating more accurate or more probative volume-rendered images by removing anatomical structures of low information quality that clutter the region of interest. Further, some embodiments herein provide a technical improvement to user interfaces associated with medical imaging systems by providing a particular display arrangement which includes the simultaneous display of a first volume-rendered image and a second volume-rendered image, and which permits the user to interact with and manipulate a user interface element in the first volume-rendered image to adjust a position of a virtual light source relative to anatomical structures displayed in the first volume-rendered image to adjust the display in the second volume-rendered image.

FIG. 1 is a diagram of an example system 100 for dynamically removing anatomical structures from a volume-rendered image based on a position of a virtual light source. As shown in FIG. 1, the system 100 may include a medical imaging system 110, a medical imaging database 120, and a network 130.

The medical imaging system 110 may be configured to acquire 3D medical imaging data of a region of interest of a subject. For example, the medical imaging system 110 may be an ultrasound system, a computed tomography (CT) system, a magnetic resonance imaging (MRI) system, an X-ray system, a positron emission tomography (PET) device, or the like.

The medical imaging database 120 may be configured to store 3D medical imaging data of a region of interest of a subject. For example, the medical imaging database 120 may be a cloud database, a hierarchical database, a network database, a centralized database, a picture archiving and communication system (PACS), or the like.

The network 130 may permit communication between the medical imaging system 110 and the medical imaging database 120. For example, the network 130 may be a local area network (LAN), a wide area network (WAN), a metropolitan area network (MAN), a cellular network, a private network, an ad hoc network, an intranet, the Internet, a fiber optic-based network, a wired network, a wireless network, or the like, and/or a combination of these or other types of networks.

The number and arrangement of the system 100 are provided as an example. In practice, the system 100 may include additional devices, fewer devices, different devices, or differently arranged devices than those shown in FIG. 1. Additionally, or alternatively, a set of devices (e.g., one or more devices) of the system 100 may be integrated into a single devices, and/or perform one or more functions described as being performed by another devices, or set of devices, of the system 100.

Figure 2:
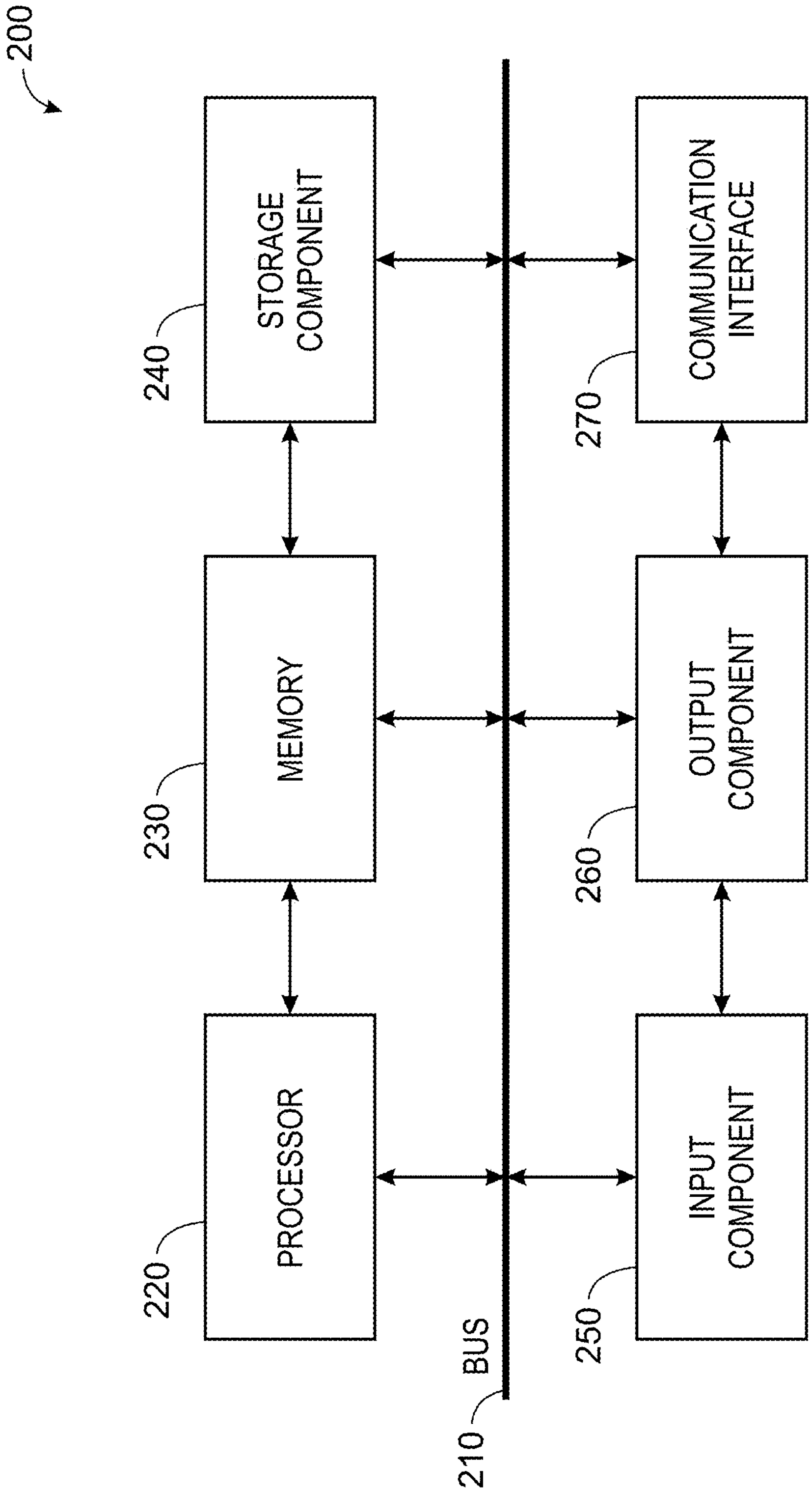
FIG. 2 is a diagram of example components of one or more devices of FIG. 1.

FIG. 2 is a diagram of example components of one or more devices 200 of FIG. 1. The device 200 may correspond to the medical imaging system 110 and/or the medical imaging database 120. As shown in FIG. 2, the device 200 may include a bus 210, a processor 220, a memory 230, a storage component 240, an input component 250, an output component 260, and a communication interface 270.

The bus 210 includes a component that permits communication among the components of the device 200. The processor 220 may be implemented in hardware, firmware, or a combination of hardware and software. The processor 220 may be a central processing unit (CPU), a graphics processing unit (GPU), an accelerated processing unit (APU), a microprocessor, a microcontroller, a digital signal processor (DSP), a field-programmable gate array (FPGA), an application-specific integrated circuit (ASIC), or another type of processing component.

The processor 220 may include one or more processors capable of being programmed to perform a function. The processor 220 may include one or more processors 220 configured to perform the operations described herein. For example, a single processor 220 may be configured to perform all of the operations described herein. Alternatively, multiple processors 220, collectively, may be configured to perform all of the operations described herein, and each of the multiple processors 220 may be configured to perform a subset of the operations descried herein. For example, a first processor 220 may perform a first subset of the operations described herein, a second processor 220 may be configured to perform a second subset of the operations described herein, etc.

The memory 230 may include a random access memory (RAM), a read only memory (ROM), and/or another type of dynamic or static storage device (e.g., a flash memory, a magnetic memory, and/or an optical memory) that stores information and/or instructions for use by the processor 220.

The storage component 240 may store information and/or software related to the operation and use of the device 200. For example, the storage component 240 may include a hard disk (e.g., a magnetic disk, an optical disk, a magneto-optic disk, and/or a solid state disk), a compact disc (CD), a digital versatile disc (DVD), a floppy disk, a cartridge, a magnetic tape, and/or another type of non-transitory computer-readable medium, along with a corresponding drive.

The input component 250 may include a component that permits the device 200 to receive information, such as via user input (e.g., a touch screen display, a keyboard, a keypad, a mouse, a button, a switch, a camera, and/or a microphone). Additionally, or alternatively, the input component 250 may include a sensor for sensing information (e.g., a global positioning system (GPS) component, an accelerometer, a gyroscope, and/or an actuator). The output component 260 may include a component that provides output information from the device 200 (e.g., a display, a speaker for outputting sound at the output sound level, and/or one or more light-emitting diodes (LEDs)).

The communication interface 270 may include a transceiver-like component (e.g., a transceiver and/or a separate receiver and transmitter) that enables the device 200 to communicate with other systems, such as via a wired connection, a wireless connection, or a combination of wired and wireless connections. The communication interface 270 may permit the device 200 to receive information from another system and/or provide information to another system. For example, the communication interface 270 may include an Ethernet interface, an optical interface, a coaxial interface, an infrared interface, a radio frequency (RF) interface, a universal serial bus (USB) interface, a Wi-Fi interface, a cellular network interface, or the like.

The device 200 may perform one or more processes described herein. The device 200 may perform these processes based on the processor 220 executing software instructions stored by a non-transitory computer-readable medium, such as the memory 230 and/or the storage component 240. A computer-readable medium may be defined herein as a non-transitory memory device. A memory device may include memory space within a single physical storage device or memory space spread across multiple physical storage devices.

The software instructions may be read into the memory 230 and/or the storage component 240 from another computer-readable medium or from another system via the communication interface 270. When executed, the software instructions stored in the memory 230 and/or the storage component 240 may cause the processor 220 to perform one or more processes described herein. Additionally, or alternatively, hardwired circuitry may be used in place of or in combination with software instructions to perform one or more processes described herein. Thus, implementations described herein are not limited to any specific combination of hardware circuitry and software.

The number and arrangement of the components of the device 200 shown in FIG. 2 are provided as an example. In practice, the device 200 may include additional components, fewer components, different components, or differently arranged components than those shown in FIG. 2. Additionally, or alternatively, a set of components (e.g., one or more components) of the device 200 may perform one or more functions described as being performed by another set of components of the device 200.

Figure 3:
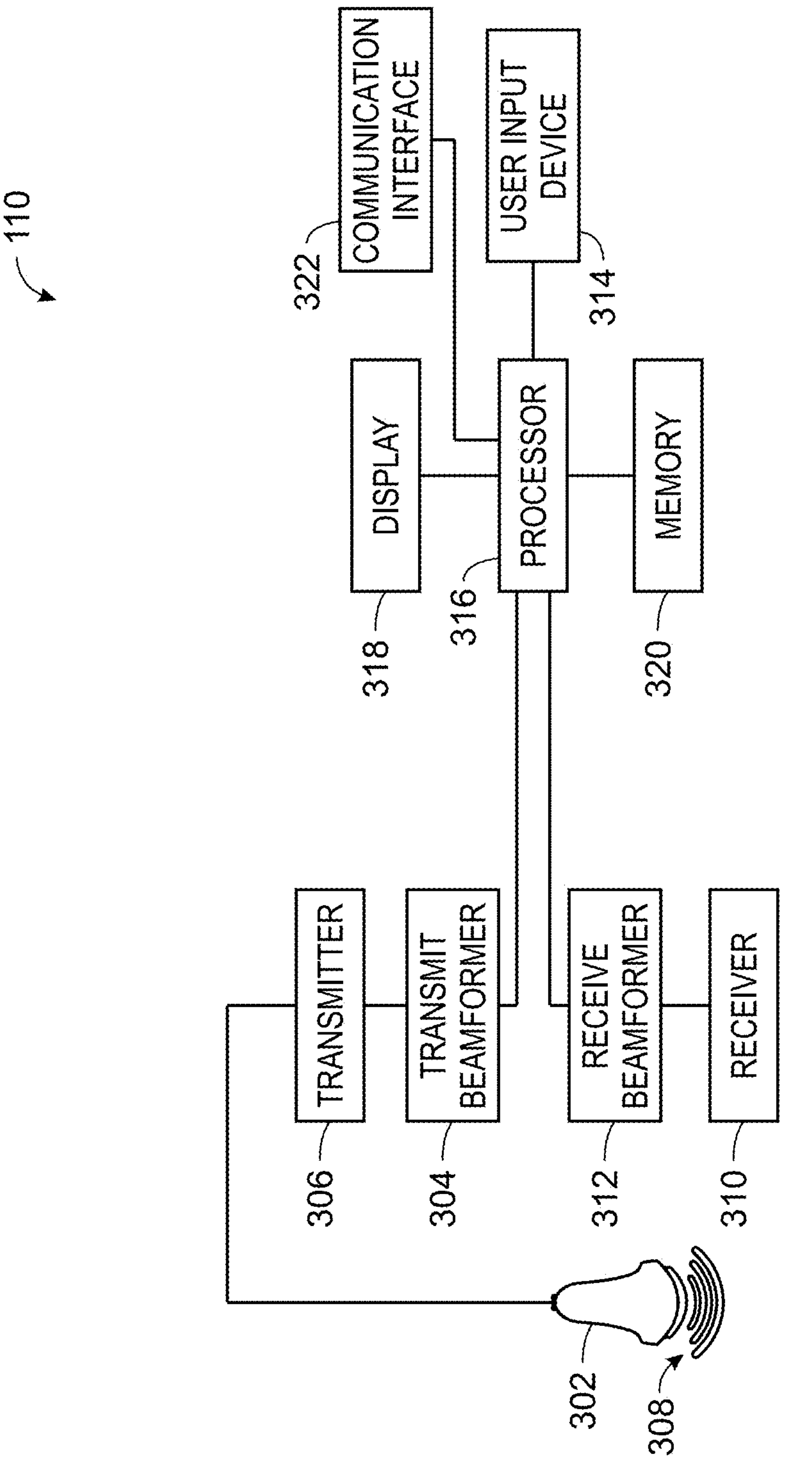
FIG. 3 is a diagram of example components of an ultrasound imaging system.

FIG. 3 is a diagram of example components of a medical imaging system 110. As shown in FIG. 3, the medical imaging system 110 may include an ultrasound probe 302, a transmit beamformer 304, a transmitter 306, elements 308 a receiver 310, a receive beamformer 312, a user input device 314, a processor 316, a display 318, a memory 320, and a communication interface 322. The foregoing components may be connected via wired or wireless connections.

The ultrasound probe 302 may be configured to acquire ultrasound data of a region of interest of a subject. For example, the ultrasound probe 302 may be a linear probe, a phase array probe, a curved linear probe coupled with a position tracking system, a mechanically steered linear array transducer, a phased array transducer, a curved linear array transducer, an electronically steered 2D transducer array, an electronic 3D (e3D) probe, an electronic 4d (e4D) probe, a low profile wearable patch version of any of the foregoing probes, or the like. According to an embodiment, the ultrasound probe 302 may be configured to generate ultrasound signals, emit the ultrasound signals towards the region of interest of a subject, receive echo ultrasound signals that are back-scattered from the region of interest of the subject, generate ultrasound data based on the echo ultrasound signals, and output the ultrasound data.

The transmit beamformer 304 may be configured to apply delay times to electrical signals provided to the elements 308 to focus corresponding ultrasound signals at the region of interest. The transmitter 306 may be configured to transmit electrical signals to the elements 308 to drive the elements 308 to emit ultrasound signals towards the region of interest. The elements 308 may be configured to receive the electrical signals from the transmitter 306, convert the electrical signals into ultrasound signals, and emit the ultrasound signals towards the region of interest. The elements 308 may be configured to receive echo ultrasound signals that are back-scattered by the region of interest, convert the echo ultrasound signals into electrical signals, and provide the electrical signals to the receiver 310. The receiver 310 may be configured to receive electrical signals from the elements 308, and provide the electrical signals to the receive beamformer 312. The receive beamformer 312 may apply delay times to the electrical signals received from the elements 308.

The user input device 314 may be configured to receive a user input, and provide the user input to the processor 316. For example, the user input device 314 may be a touch screen display, a keyboard, a keypad, a mouse, a button, a switch, a microphone, or the like. Additionally, or alternatively, the user input device 314 may be configured to sense information. For example, the user input device 314 may sense information from an electro-magnetic positioning system, an inertial measurement system, an accelerometer, a gyroscope, an actuator, or the like.

The processor 316 may be configured to perform the operations as described herein. For example, the processor 316 may be a central processing unit (CPU), a graphics processing unit (GPU), an accelerated processing unit (APU), a microprocessor, a microcontroller, a digital signal processor (DSP), a field-programmable gate array (FPGA), an application-specific integrated circuit (ASIC), or another type of processing component. The processor 316 may be implemented in hardware, firmware, or a combination of hardware and software. The processor 316 may include one or more processors 316 configured to perform the operations described herein. For example, a single processor 316 may be configured to perform all of the operations described herein. Alternatively, multiple processors 316, collectively, may be configured to perform all of the operations described herein, and each of the multiple processors 316 may be configured to perform a subset of the operations descried herein. For example, a first processor 316 may perform a first subset of the operations described herein, a second processor 316 may be configured to perform a second subset of the operations described herein, etc.

The processor 316 may be configured to control the ultrasound probe 302 to acquire ultrasound data. The processor 316 may be configured to control which of the elements 308 are active, and control the shape of a beam emitted from the ultrasound probe 302. The processor 316 may generate ultrasound images for display. For example, the processor 316 may generate B-mode images, color Doppler images, M-mode images, color M-mode images, or the like. The ultrasound images may be 3D images, 2D images, single plane images, bi-plane images, three-plane images, multi-plane images, or the like. The ultrasound images may correspond to various anatomical planes (e.g., sagittal, coronal, and transverse) of the region of interest.

The display 318 may be configured to display information. For example, the display 318 may be a monitor, an LED display, a cathode ray tube, a projector display, a touchscreen, tablet computer, mobile phone, or the like. The display 318 may display ultrasound images based on the ultrasound data in real-time. For example, the display 318 may display the ultrasound images within one second, two seconds, five seconds, etc., of the ultrasound data being acquired by the ultrasound probe 302.

The memory 320 may be configured to store information and/or instructions for use by the processor 316. The memory 320 may be a non-transitory computer-readable medium. For example, the memory 320 may be a RAM, a ROM, and/or another type of dynamic or static storage device (e.g., a flash memory, a magnetic memory, and/or an optical memory) that stores information and/or instructions for use by the processor 316. The memory 320 may be configured to store instructions that, when executed by the processor 316, cause the processor 316 to perform the operations described herein.

The communication interface 322 may be configured to enable the processor 316 to communicate with other systems, such as via a wired connection, a wireless connection, or a combination of wired and wireless connections. For example, the communication interface 322 may include an Ethernet interface, an optical interface, a coaxial interface, an infrared interface, an RF interface, a USB interface, a Wi-Fi interface, a cellular network interface, or the like.

The number and arrangement of the components of the medical imaging system 110 shown in FIG. 3 are provided as an example. In practice, the medical imaging system 110 may include additional components, fewer components, different components, or differently arranged components than those shown in FIG. 3. Additionally, or alternatively, a set of components (e.g., one or more components) of the medical imaging system 110 may perform one or more functions described as being performed by another set of components of the medical imaging system 110.

Figure 4:
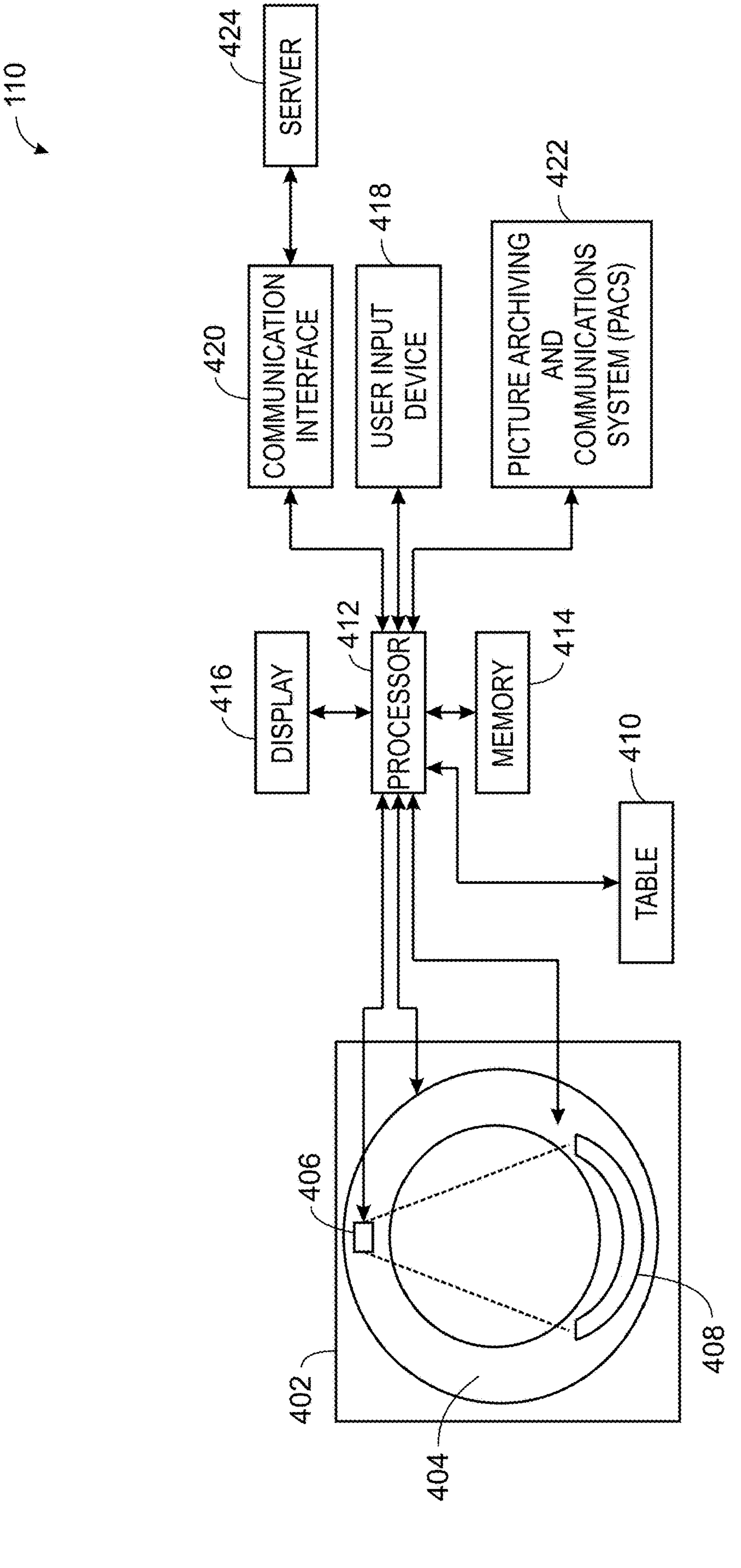
FIG. 4 is a diagram of a computed tomography imaging system.

FIG. 4 is a diagram of example components of a medical imaging system 110. As shown in FIG. 4, the medical imaging system 110 may include a gantry 402, a rotational frame 404, an X-ray source 406, an X-ray detector 408, a table 410, a processor 412, a memory 414, a display 416, a user input device 418, a communication interface 420, a picture archiving and communications system (PACS) 422, and a server 424.

The processor 412 may be configured to control operations of the medical imaging system 110. For example, the processor 412 may be a CPU, a GPU, an APU, a microprocessor, a microcontroller, a DSP, an FPGA, an ASIC, or the like. The processor 412 may be implemented in hardware, firmware, or a combination of hardware and software. The processor 412 may include one or more processors 412 configured to perform the operations described herein. For example, a single processor 412 may be configured to perform all of the operations described herein. Alternatively, multiple processors 412, collectively, may be configured to perform all of the operations described herein, and each of the multiple processors 412 may be configured to perform a subset of the operations descried herein. For example, a first processor 412 may perform a first subset of the operations described herein, a second processor 412 may be configured to perform a second subset of the operations described herein, etc.

The processor 412 may be configured to control the gantry 402, movement of the rotational frame 404, the X-ray source 406, the X-ray detector 408, and movement of the table 410.

The memory 414 may be configured to store information and/or instructions for use by the processor 412. The memory 414 may be a non-transitory computer-readable medium. For example, the memory 414 may be a RAM, a ROM, a flash memory, a magnetic memory, an optical memory, or the like. The memory 414 may be configured to store instructions that, when executed by the processor 412, cause the processor 412 to perform the operations described herein.

The display 416 may be configured to display information. For example, the display 416 may be a monitor, an LED display, a cathode ray tube, a projector display, a touchscreen, tablet computer, mobile phone, or the like.

The user input device 418 may be configured to receive a user input, and provide the user input to the processor 412. For example, the user input device 418 may be a touch screen display, a keyboard, a keypad, a mouse, a button, a switch, a microphone, or the like. Additionally, or alternatively, the user input device 418 may be configured to sense information. For example, the user input device 418 may sense information from an electro-magnetic positioning system, an inertial measurement system, an accelerometer, a gyroscope, an actuator, or the like.

The communication interface 420 may be configured to enable the processor 412 to communicate with other devices, such as via a wired connection, a wireless connection, or a combination of wired and wireless connections.

For example, the communication interface 420 may include an Ethernet interface, an optical interface, a coaxial interface, an infrared interface, an RF interface, a USB interface, a Wi-Fi interface, a cellular network interface, or the like. The PACS 422 may be configured to communicate with external systems and/or networks to permit users at various locations to access the medical image. The server 424 may be configured to store one or more models as described herein. For example, the server 424 may be an on-premises server, a cloud server, a virtual machine, or the like.

The number and arrangement of the components of the medical imaging system 110 shown in FIG. 4 are provided as an example. In practice, the medical imaging system 110 may include additional components, fewer components, different components, or differently arranged components than those shown in FIG. 4. Additionally, or alternatively, a set of components (e.g., one or more components) of the medical imaging system 110 may perform one or more functions described as being performed by another set of components of the medical imaging system 110.

Figure 5:
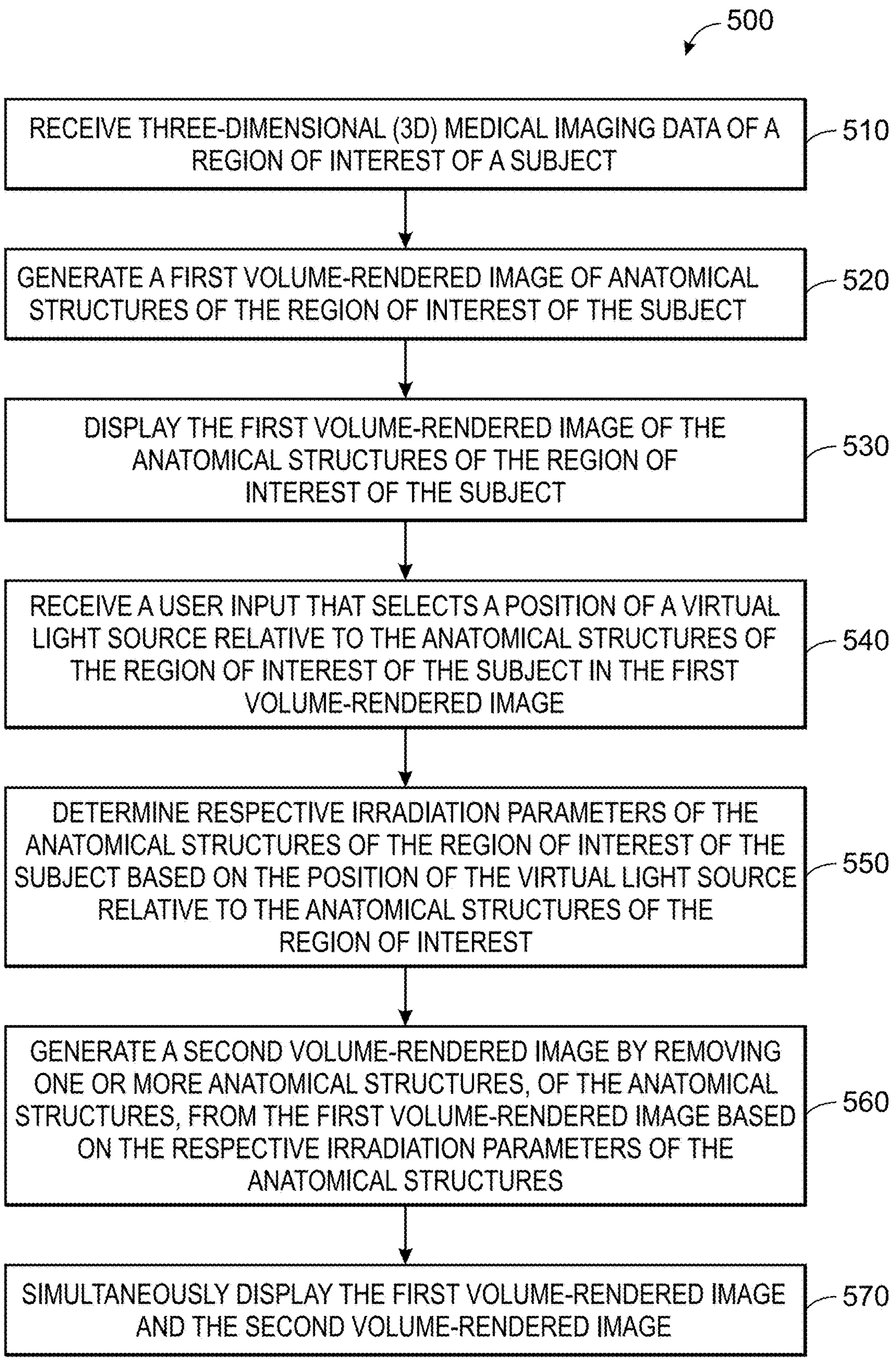
FIG. 5 is a flowchart of an example process for dynamically removing anatomical structures from a volume-rendered image based on a position of a virtual light source.

FIG. 5 is a flowchart of an example process 500 for dynamically removing anatomical structures from a volume-rendered image based on a position of a virtual light source. According to an embodiment, the medical imaging system 110 may perform one or more operations of the process 500 of FIG. 5. Alternatively, one or more other devices may perform one or more operations of the process 500 of FIG. 5.

As shown in FIG. 5, the process 500 may include receiving three-dimensional (3D) medical imaging data of a region of interest of a subject (operation 510). For example, the medical imaging system 110 may receive 3D medical imaging data of a region of interest of a subject. According to an embodiment, the 3D medical imaging data may be any type of medical imaging data. For example, the 3D medical imaging data may be ultrasound data, CT data, MRI data, X-ray data, PET data, or the like. The region of interest may be any anatomical region of the subject. For example, the region of interest may be the heart, the liver, the pancreas, the brain, or the like. The subject may be any type of subject to be imaged. For example, the subject may be a person, an animal, a phantom, or the like. According to an embodiment, the 3D medical imaging data may include voxels. Each voxel may include one or more values. For example, a voxel may include an intensity value, a color value, an opacity value, or the like. According to an embodiment, the medical imaging system 110 may receive the 3D medical imaging data based on performing a scan of the subject. In this case, the medical imaging system 110 may receive the 3D medical imaging data in substantially real-time. As used herein, the 3D medical imaging data being received in "substantially real-time" may refer to the 3D medical imaging data being received within a threshold amount of time of the 3D medical imaging data being acquired (e.g., 10 seconds, 1 minute, 5 minutes, etc.) via a scan. Alternatively, the medical imaging system 110 may receive the 3D medical imaging data from the medical imaging database 120. For example, the medical imaging system 110 may request the 3D medical imaging data from the medical imaging database 120, and receive the 3D medical imaging data based on the request.

As further shown in FIG. 5, the process 500 may include generating a first volume-rendered image of anatomical structures of the region of interest of the subject (operation 520). For example, the medical imaging system 110 may generate a first volume-rendered image of anatomical structures of the region of interest of the subject. According to an embodiment, the medical imaging system 110 may generate the first volume-rendered image using the 3D medical imaging data and a rendering technique. For example, the rendering technique may be a ray-tracing technique, a ray casting technique, a photon mapping technique, a path tracing technique, a scanline rendering technique, or the like. According to an embodiment, the anatomical structures may be any type of structures of the subject. For example, in the case where the region of interest is the heart, the anatomical structures may be the left atrial appendage, the mitral valve, the aortic valve, the pulmonary valve, the tricuspid valve, tissue, or the like. Additionally, or alternatively, the anatomical structures may include a stent, a mitral valve clip, a pacemaker, or the like.

As further shown in FIG. 5, the process 500 may include displaying the first volume-rendered image of the anatomical structures of the region of interest of the subject (operation 530). For example, the medical imaging system 110 may display the first volume-rendered image of the anatomical structures of the region of interest of the subject. According to an embodiment, the medical imaging system 110 may display the first volume-rendered image on a first area of a display.

As further shown in FIG. 5, the process 500 may include receiving a user input that selects a position of a virtual light source relative to the anatomical structures of the region of interest of the subject in the first volume-rendered image (operation 540). For example, the medical imaging system 110 may receive a user input that selects a position of a virtual light source relative to the anatomical structures of the region of interest. According to an embodiment, the virtual light source may irradiate the anatomical structures of the region of interest. For example, the virtual light source may include an irradiation configuration that permits the virtual light source to irradiate the anatomical structures of the region of interest. The irradiation configuration may include a shape of the virtual light source, a size of the virtual light source, an irradiation intensity of the virtual light source, an irradiation pattern of the virtual light source, or the like. According to an embodiment, a user may interact with a user interface to select a position of the virtual light source relative to the anatomical structures of the region of interest of the subject. For example, the user may interact with the user interface to select a position of the virtual light source by adjusting a location of the virtual light source, an orientation of the virtual light source, or the like.

As further shown in FIG. 5, the process 500 may include determining respective irradiation parameters of the anatomical structures of the region of interest of the subject based on the position of the virtual light source relative to the anatomical structures of the region of interest (operation 550). For example, the medical imaging system 110 may determine respective irradiation parameters of the anatomical structures of the region of interest of the subject based on the position of the virtual light source relative to the anatomical structures of the region of interest. According to an embodiment, an irradiation parameter may identify the extent to which an anatomical structure is irradiated. For example, an irradiation parameter may be irradiance, which may be a density of radiation incident on a given surface of an anatomical structure. As another example, an irradiation parameter may be radiance, which may be a flux density of radiant energy per unit solid angle and per unit projected area of radiating surface of an anatomical structure. The medical imaging system 110 may determine a respective irradiation parameter for each of the anatomical structures displayed in the first volume-rendered image.

According to an embodiment, the medical imaging system 110 may generate a 3D data structure based on the 3D medical imaging data of the region of interest of the subject. The 3D data structure may store an irradiance parameter for each position of the 3D medical imaging data. For example, the medical imaging system 110 may trace light energy from the virtual light source in every direction through the 3D medical imaging data, and determine an irradiance parameter at any position with the 3D medical imaging data. For instance, the medical imaging system 110 may treat the 3D medical imaging data as a translucent material, and trace light energy from the virtual light source in every direction through the 3D medical imaging data. Further, the medical imaging system 110 may evaluate absorption, scattering, and reflection of light to determine the propagation of light energy throughout the 3D medical imaging data. The medical imaging system 110 may store the determined irradiance parameters in the 3D data structure. Further, the medical imaging system 110 may use the 3D data structure to determine which anatomical structures are shown, or not shown, in the second volume-rendered image, as described below.

As further shown in FIG. 5, the process 500 may include generating a second volume-rendered image by removing one or more anatomical structures, of the anatomical structures, from the first volume-rendered image based on the respective irradiation parameters of the anatomical structures (operation 560). For example, the medical imaging system 110 may generate a second volume-rendered image by removing one or more anatomical structures, of the anatomical structures, from the first volume-rendered image based on the respective irradiation parameters of the anatomical structures. According to an embodiment, the second volume-rendered image may be a volume-rendered image that is similar to the first volume-rendered image except that one or more anatomical structures are removed. According to an embodiment, the medical imaging system 110 may compare an irradiation parameter of an anatomical structure to an irradiation parameter threshold, and selectively remove the anatomical structure in the first volume-rendered image based on whether the irradiation parameter satisfies the irradiation parameter threshold. For example, if the irradiation parameter is less than the irradiation parameter threshold, then the medical imaging system 110 may remove the anatomical structure in the first volume-rendered image. Alternatively, as another example, if the irradiation parameter is greater than, or equal to, the irradiation parameter threshold, then the medical imaging system 110 may maintain the anatomical structure in the first volume-rendered image. According to an embodiment, the medical imaging system 110 may entirely remove the anatomical structure from the first volume-rendered image to generate the second volume-rendered image. In this case, the anatomical structure might be non-visible in the second volume-rendered image. Alternatively, the medical imaging system 110 may partially remove the anatomical structure from the first volume-rendered image to generate the second volume-rendered image. In this case, the anatomical structure may be partially visible in the second volume-rendered image. For example, the medical imaging system 110 may adjust an opacity value of voxels corresponding to the anatomical structure such that the anatomical structure is opaque, or more opaque. According to an embodiment, the medical imaging system 110 may generate the second volume-rendered image by removing one or more anatomical structures, of the anatomical structures, from the first volume-rendered image using an AI model. For example, the AI model may be a decision tree (e.g., a classification tree, a regression tree, or the like), a linear regression model, a neural network (e.g., a deep neural network (DNN), a convolutional neural network (CNN), a recurrent neural network (RNN), or the like), a logistic regression model, a support vector machine, or the like. In this case, the medical imaging system 110 may input the first volume-rendered image and information identifying the respective irradiation parameters into the AI model, and determine one or more anatomical structures to remove based on an output of the AI model. According to an embodiment, the medical imaging system 110 may generate the second volume-rendered image by removing one or more anatomical structures, of the anatomical structures, from the first volume-rendered image using information identifying a target anatomical structure. For example, the medical imaging system 110 may receive a user input that selects a target anatomical structure. In this case, the medical imaging system 110 may generate the second volume-rendered image by removing one or more anatomical structures, of the anatomical structures, from the first volume-rendered image based on the user input. For instance, the medical imaging system 110 may not remove the target anatomical structure, and might remove one or more anatomical structures that partially, or entirely, occlude the target anatomical structure.

As further shown in FIG. 5, the process 500 may include simultaneously displaying the first volume-rendered image and the second volume-rendered image (operation 570). For example, the medical imaging system 110 may simultaneously display the first volume-rendered image and the second volume-rendered image. According to an embodiment, the medical imaging system 110 may display the first volume-rendered image in a first area of a display, and may display the second volume-rendered image in a second area of the display. For example, the first area of the display and the second area of the display may be adjacent to each other. The medical imaging system 110 may simultaneously display the first volume-rendered image and the second volume-rendered image. In this way, the second volume-rendered image appears similar to the first volume-rendered image in that both of the first volume-rendered image and the second volume-rendered image display one or more common anatomical structures, except that the second volume-rendered image does not display one or more anatomical structures that were removed from the first volume-rendered image.

Although FIG. 5 depicts particular operations and a particular order of operations, it should be understood that the process 500 may include different operations, more operations, less operations, and/or a different order of operations in other embodiments.

Figure 6:
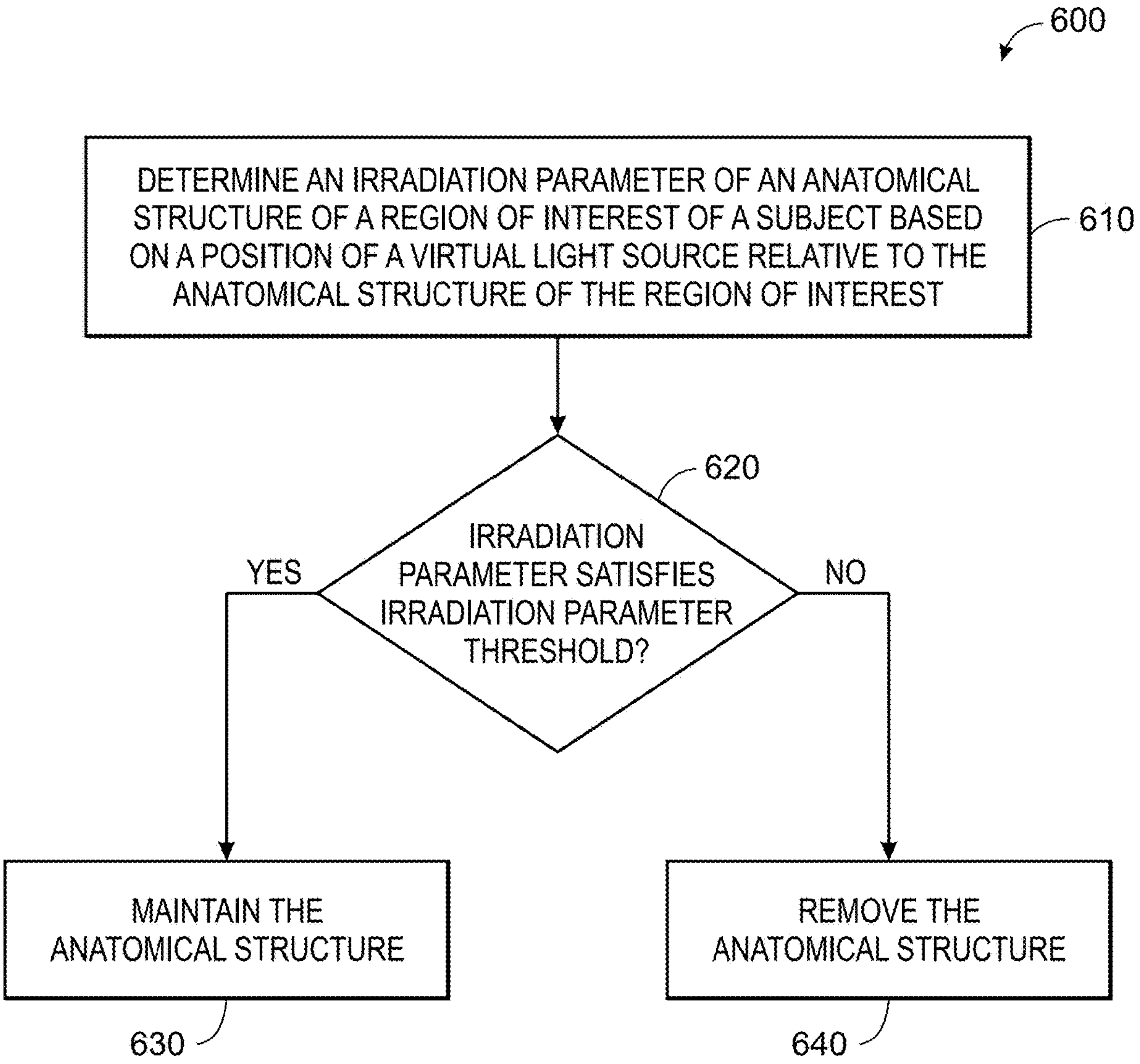
FIG. 6 is a flowchart of an example process for selectively removing an anatomical structure from a volume-rendered image based on an irradiation parameter of the anatomical structure.

FIG. 6 is a flowchart of an example process 600 for selectively removing an anatomical structure from a volume-rendered image based on an irradiation parameter of the anatomical structure. According to an embodiment, the medical imaging system 110 may perform one or more operations of the process 600 of FIG. 6. Alternatively, one or more other devices may perform one or more operations of the process 600 of FIG. 6.

As shown in FIG. 6, the process 600 may include determine an irradiation parameter of an anatomical structure of a region of interest of a subject based on a position of a virtual light source relative to the anatomical structure of the region of interest (operation 610). For example, the medical imaging system 110 may determine an irradiation parameter of an anatomical structure of a region of interest of a subject based on a position of a virtual light source relative to the anatomical structure of the region of interest in a similar manner as described above in connection with operation 550 of FIG. 5.

As further shown in FIG. 6, the process 600 may include determining whether the irradiation parameter satisfies an irradiation parameter threshold (operation 620). For example, the medical imaging system 110 may determine whether the irradiation parameter satisfies an irradiation parameter threshold. The medical imaging system 110 may compare the irradiation parameter to a corresponding irradiation parameter threshold. For example, if the irradiation parameter is irradiance, then the irradiation parameter threshold may be an irradiance threshold. As another example, if the irradiation parameter is radiance, then the irradiation parameter may be a radiance threshold. The medical imaging system 110 may determine whether the irradiation parameter satisfies the threshold based on determining whether the irradiation parameter is greater than the irradiation parameter threshold, greater than or equal to the irradiation parameter threshold, equal to the irradiation parameter threshold, less than or equal to the irradiation parameter threshold, or less than the irradiation parameter threshold.

As further shown in FIG. 6, if the irradiation parameter satisfies the irradiation parameter threshold (operation 620—YES), then the process 600 may include maintaining the anatomical structure (operation 630). For example, the medical imaging system 110 may maintain the anatomical structure in the second volume-rendered image based on determining that the irradiation parameter satisfies the irradiation parameter threshold. In this case, the medical imaging system 110 may simultaneously display the first volume-rendered image and the second volume-rendered image, and the anatomical structure may be visible in both of the first volume-rendered image and the second volume-rendered image.

As further shown in FIG. 6, if the irradiation parameter does not satisfy the irradiation parameter threshold (operation 620—NO), then the process 600 may include removing the anatomical structure (operation 640). For example, the medical imaging system 110 may remove the anatomical structure in the second volume-rendered image based on determining that the irradiation parameter does not satisfy the irradiation parameter threshold. In this case, the medical imaging system 110 may simultaneously display the first volume-rendered image and the second volume-rendered image, and the anatomical structure may be visible in the first volume-rendered image and might not be visible in the second volume-rendered image.

Although FIG. 6 depicts particular operations and a particular order of operations, it should be understood that the process 600 may include different operations, more operations, less operations, and/or a different order of operations in other embodiments.

Figure 7:
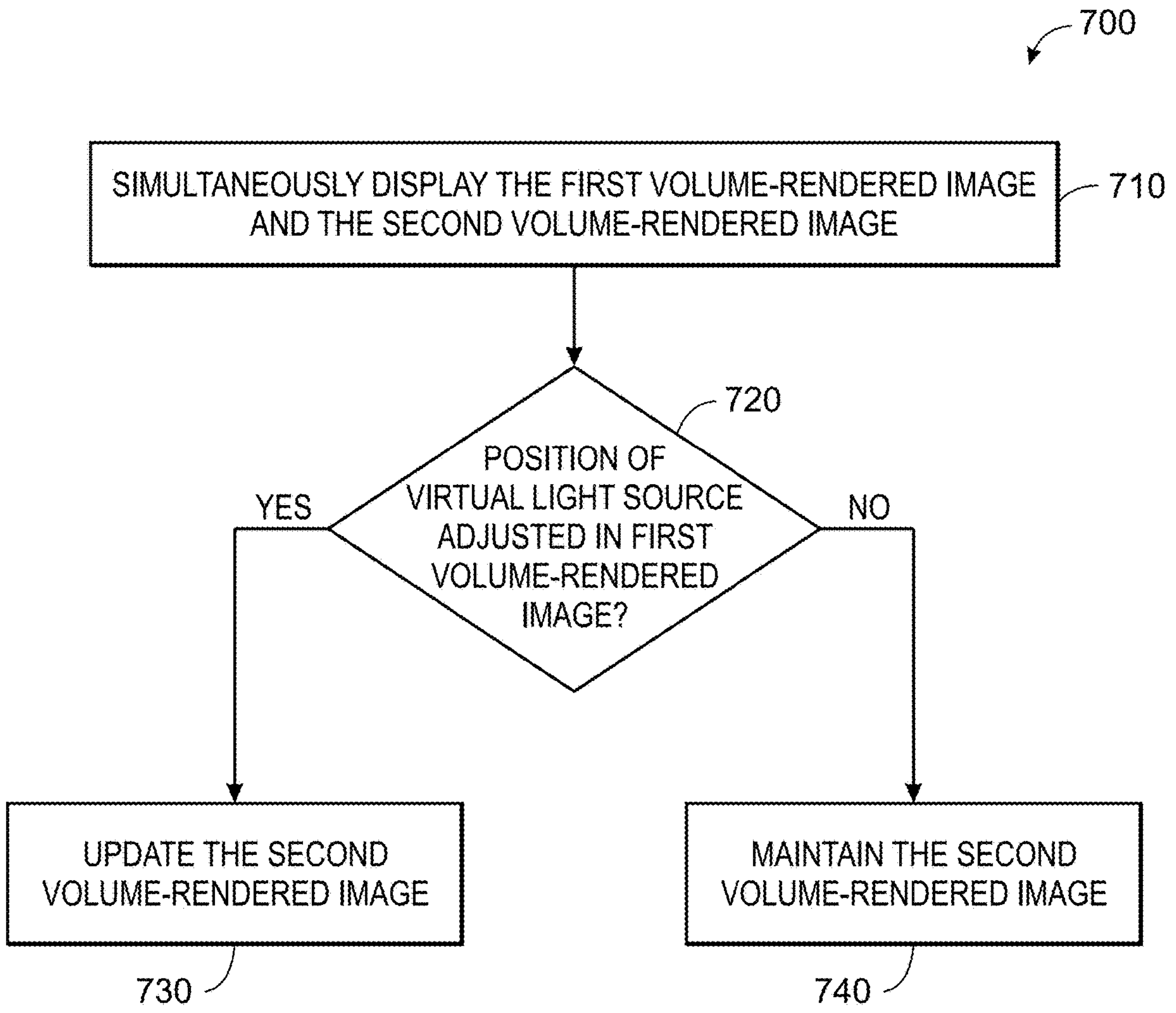
FIG. 7 is a flowchart of an example process for dynamically updated a second volume-rendered image based on an adjustment to a position of a virtual light source in a first volume-rendered image.

FIG. 7 is a flowchart of an example process 700 for dynamically updated a second volume-rendered image based on an adjustment to a position of a virtual light source in a first volume-rendered image. According to an embodiment, the medical imaging system 110 may perform one or more operations of the process 700 of FIG. 7. Alternatively, one or more other devices may perform one or more operations of the process 700 of FIG. 7.

As shown in FIG. 7, the process 700 may include simultaneously displaying a first volume-rendered image and a second volume-rendered image (operation 710). For example, the medical imaging system 110 may simultaneously display a first volume-rendered image and a second volume-rendered image in a similar manner as described above in connection with operation 570 of FIG. 5.

As further shown in FIG. 7, the process 700 may include determining whether a position of a virtual light source is adjusted in the first volume-rendered image (operation 720). For example, the medical imaging system 110 may determine whether a position of a virtual light source is adjusted in the first volume-rendered image. A user may interact with a user interface to adjust a position of the virtual light source, or the virtual light sources, in the first volume-rendered image. For instance, the user may move the virtual light source relative to the anatomical structures displayed in the first volume-rendered image. In this case, the respective irradiation parameters of the anatomical structures may change based on the positioning of the virtual light source relative to the anatomical structures. The medical imaging system 110 may detect a user input that adjusts a position of a virtual light source.

As further shown in FIG. 7, if the position of the virtual light source is adjusted in the first volume-rendered image (operation 720—YES), then the process 700 may include updating the second volume-rendered image (operation 730). For example, the medical imaging system 110 update the second volume-rendered image based on determining that the position of the virtual light source is adjusted in the first volume-rendered image. The medical imaging system 110 may update the second volume-rendered image by, for example, performing one or more of operations 550-570 of FIG. 5. That is, the medical imaging system 110 may determine respective irradiation parameters of the anatomical structures of the region of interest based on the adjusted position of the virtual light source relative to the anatomical structures of the region of interest in the first volume-rendered image, and selectively maintain or remove the anatomical structures based on the respective irradiation parameters.

As further shown in FIG. 7, if the position of the virtual light source is not adjusted in the first volume-rendered image (operation 720—NO), then the process 700 may include maintaining the second volume-rendered image (operation 740). For example, the medical imaging system 110 maintain the second volume-rendered image based on determining that the position of the virtual light source has not been adjusted in the first volume-rendered image.

Although FIG. 7 depicts particular operations and a particular order of operations, it should be understood that the process 700 may include different operations, more operations, less operations, and/or a different order of operations in other embodiments.

Figure 8A:
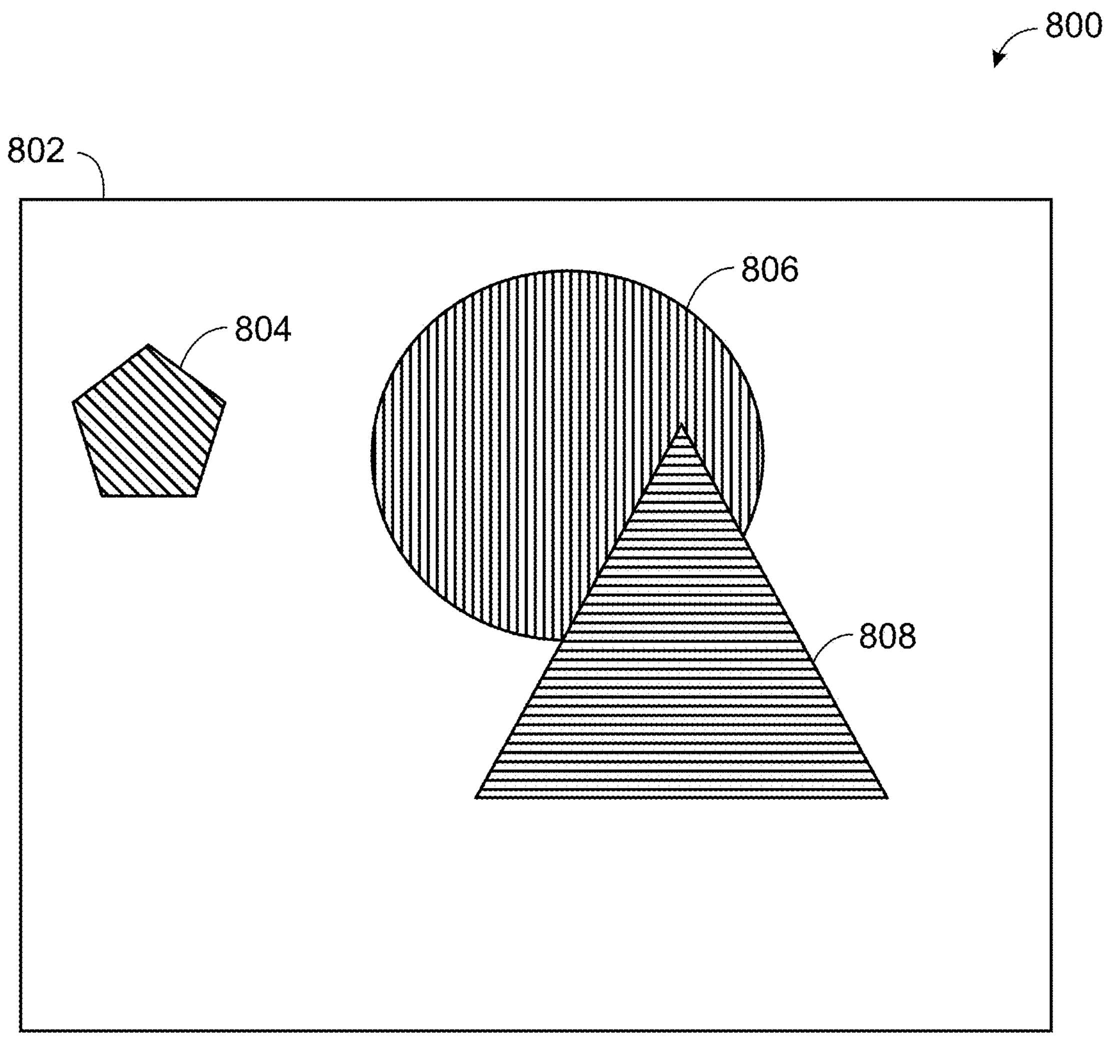
FIGS. 8A-8C are diagrams of an example display of dynamically removing anatomical structures from a volume-rendered image based on a position of a virtual light source.
Figure 8B:
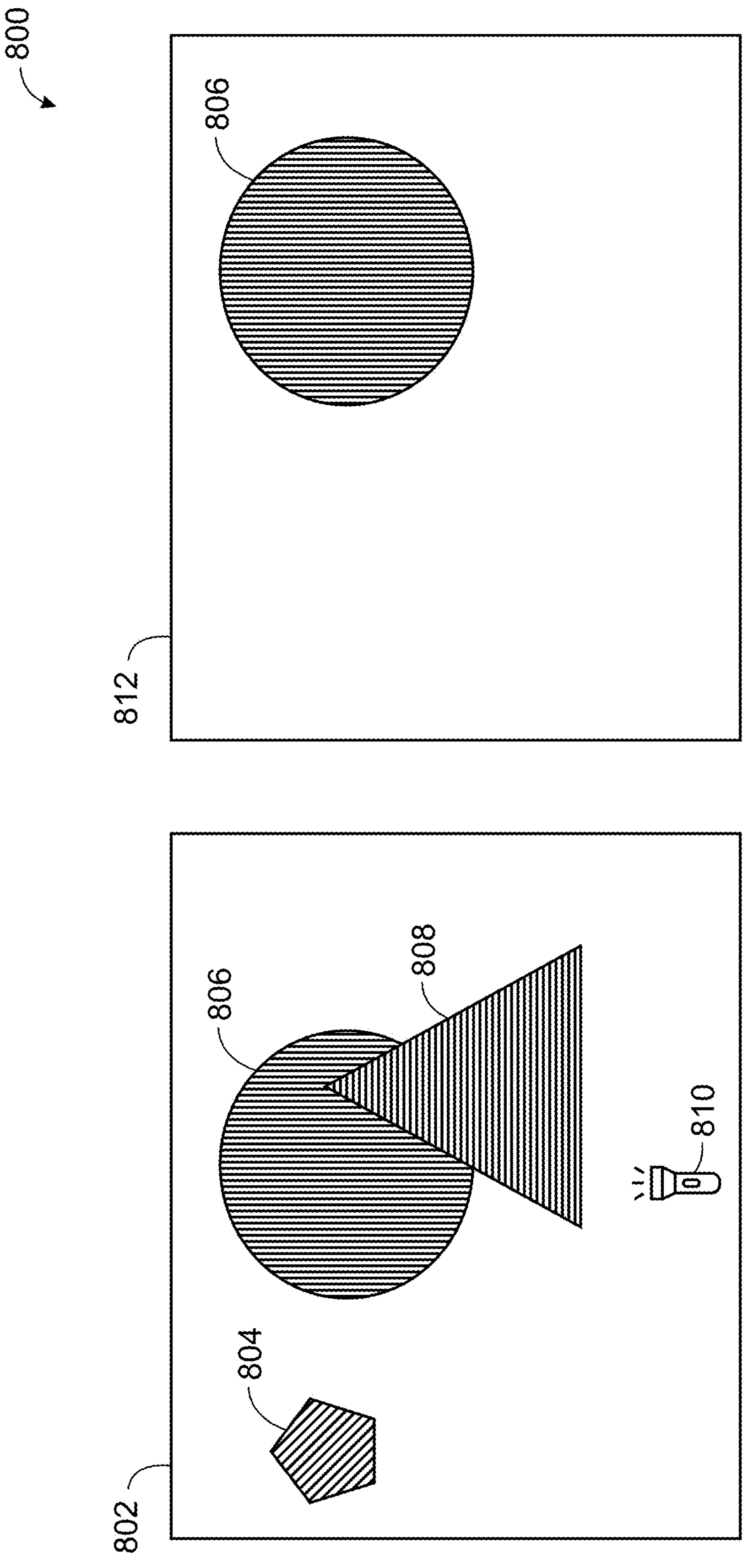
Figure 8C:
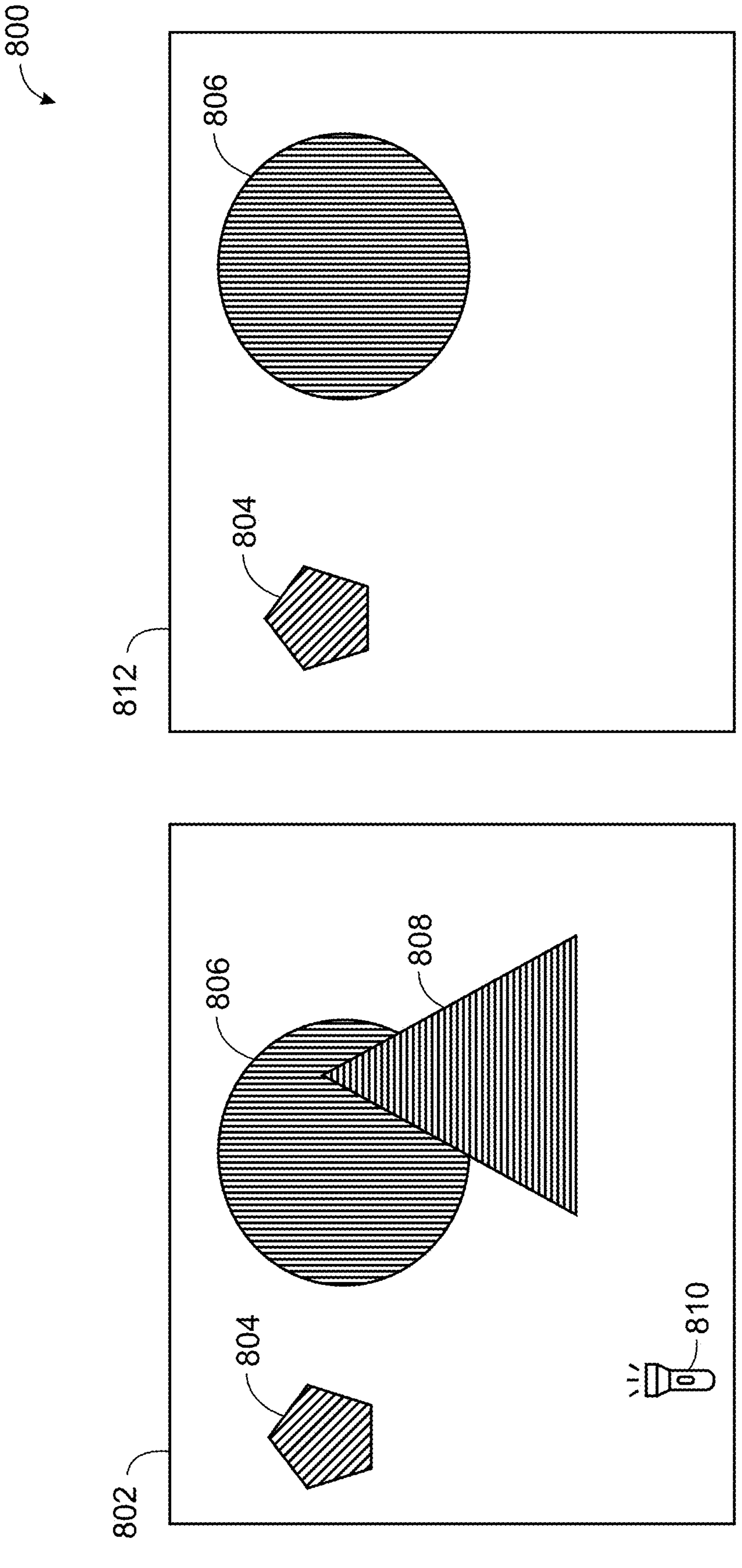

FIGS. 8A-8C are diagrams of an example display 800 of dynamically removing anatomical structures from a volume-rendered image based on a position of a virtual light source. As shown in FIG. 8A, a first volume-rendered image 802 may include a first anatomical structure 804, a second anatomical structure 806, and a third anatomical structure 808. As shown in FIG. 8A, the third anatomical structure 808 may partially occlude the second anatomical structure 806. As shown in FIG. 8B, the medical imaging system 110 may simultaneously display the first volume-rendered image 802 and a second volume-rendered image 812. As shown in FIG. 8B, the medical imaging system 110 may display a user interface element 810 corresponding to a virtual light source in the first volume-rendered image 802. The medical imaging system 110 may perform, for example, operations 550 through 570 of FIG. 5 to simultaneously display the first volume-rendered image 802 and the second volume-rendered image 812. In this case, assume that the respective irradiation parameters of the first anatomical structure 804 and the third anatomical structure 808 do not satisfy respective irradiation parameter thresholds. As shown in FIG. 8B, the medical imaging system 110 may remove the first anatomical structure 804 and the third anatomical structure 808 from the first volume-rendered image 802 to generate the second volume-rendered image 812. In this way, the second volume-rendered image 812 may display only the second anatomical structure 806 instead of all of the first anatomical structure 804, the second anatomical structure 806, and the third anatomical structure 808 as shown in the first volume-rendered image 802. Accordingly, the user can more readily assess the second anatomical structure 806 because, at least, the third anatomical structure 808 has been removed from the first volume-rendered image 802. As shown in FIG. 8C, a user may interact with the user interface element 810 corresponding to the virtual light source in the first volume-rendered image 802, such as by moving the user interface element 810 to the left side of the first volume-rendered image 802. In this case, the adjusted position of the virtual light source may affect the respective irradiation parameters of the first anatomical structure 804, the second anatomical structure 806, and the third anatomical structure 808. Accordingly, the medical imaging system 110 may perform, at least, operations 550 through 570 of FIG. 5 to update the second volume-rendered image 812. In this case, as shown in FIG. 8C, the medical imaging system 110 may display the first anatomical structure 804 and the second anatomical structure 806, and may remove the third anatomical structure 808 from the first volume-rendered image 802.

Figure 9:
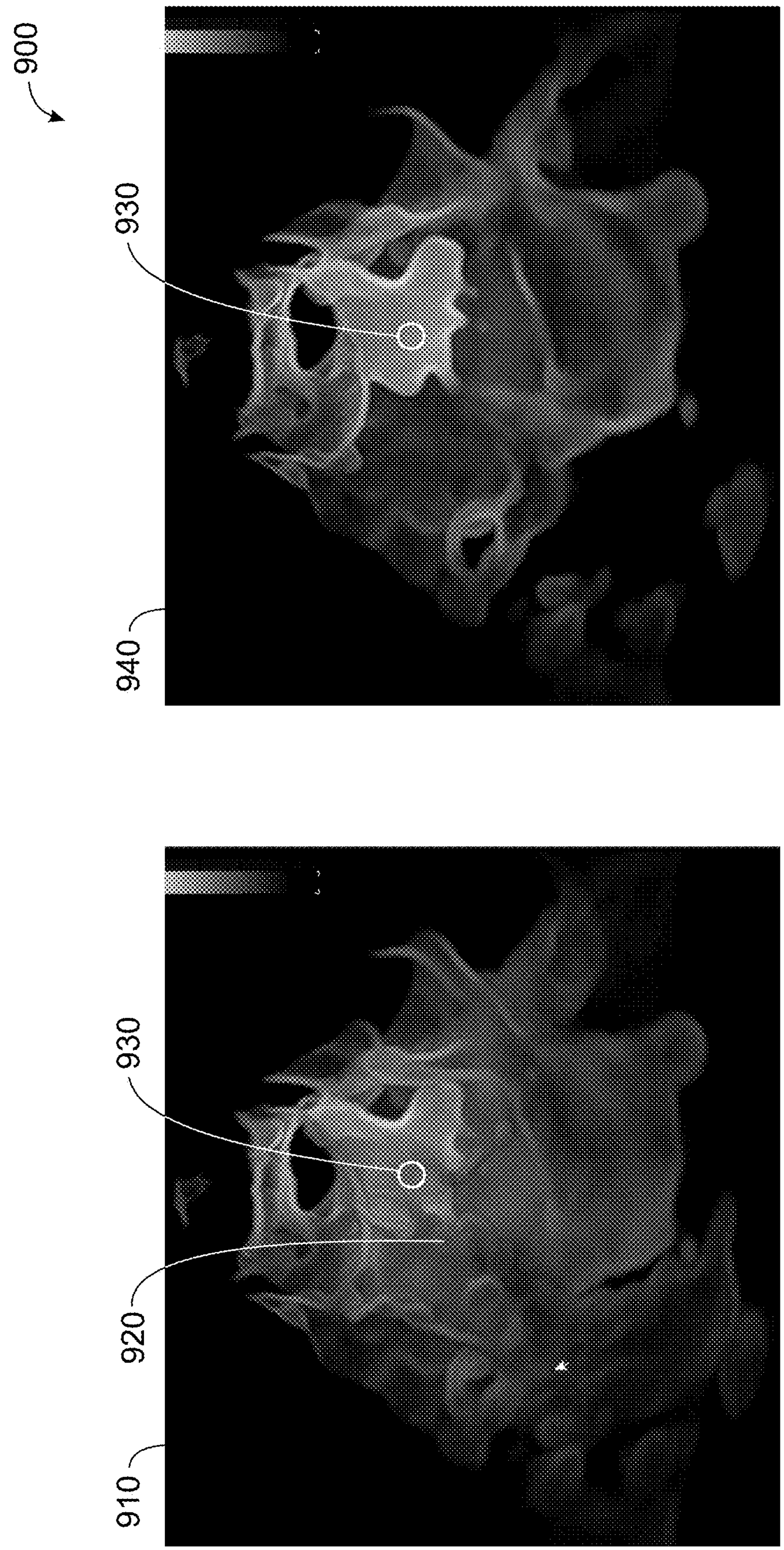
FIG. 9 is a diagram of an example display of dynamically removing anatomical structures from a volume-rendered image based on a position of a virtual light source.

FIG. 9 is a diagram of an example display 900 of dynamically removing anatomical structures from a volume-rendered image based on a position of a virtual light source. As shown in FIG. 9, the medical imaging system 110 may simultaneously display a first volume-rendered image 910 of a region of interest (e.g., left atrium) of a subject and a second volume-rendered image 940 of the region of interest of the subject. As shown, the first volume-rendered image 910 may include a first anatomical structure 920 (e.g., tissue) and a second anatomical structure 930 (e.g., a left atrial appendage). In this case, assume that the user is interested in viewing the second anatomical structure 930 and is not interested in viewing the first anatomical structure 920. The medical imaging system 110 may perform, at least, operations 550 through 570 of FIG. 5 to update the second volume-rendered image 940. As shown, the medical imaging system 110 may remove the first anatomical structure 920 from the first volume-rendered image 910 to generate the second volume-rendered image 940. In this way, the second volume-rendered image 940 may display only the second anatomical structure 930 instead of both of the first anatomical structure 920 and the second anatomical structure 930.

Although the embodiments herein describe the utilization of a single virtual light source, it should be understood that other embodiments may include multiple virtual light sources. In these cases, the medical imaging system 110 may determine irradiation parameters of anatomical structures based on irradiation from the multiple virtual light sources.

Although the embodiments herein describe the simultaneously displaying of the first volume-rendered image and the second volume-rendered image, it should be understood that other embodiments may include the display of a single volume-rendered image. For instance, the user may manipulate a user interface element corresponding to a virtual light source in the volume-rendered image, and the medical imaging system 110 may selectively remove various anatomical structures from the volume-rendered image based on the position of the virtual light source relative to the anatomical structures.

Embodiments of the present disclosure shown in the drawings and described above are example embodiments only and are not intended to limit the scope of the appended claims, including any equivalents as included within the scope of the claims. Various modifications are possible and will be readily apparent to the skilled person in the art. It is intended that any combination of non-mutually exclusive features described herein are within the scope of the present invention. That is, features of the described embodiments can be combined with any appropriate aspect described above and optional features of any one aspect can be combined with any other appropriate aspect. Similarly, features set forth in dependent claims can be combined with non-mutually exclusive features of other dependent claims, particularly where the dependent claims depend on the same independent claim. Single claim dependencies may have been used as practice in some jurisdictions require them, but this should not be taken to mean that the features in the dependent claims are mutually exclusive.

What is claimed is:

1. A system comprising:

a memory configured to store instructions; and one or more processors configured to execute the instructions to:

receive three-dimensional (3D) medical imaging data of a region of interest of a subject;

generate a first volume-rendered image of anatomical structures of the region of interest of the subject;

display the first volume-rendered image of the anatomical structures of the region of interest of the subject;

receive a user input that selects a position of a virtual light source relative to the anatomical structures of the region of interest of the subject in the first volume-rendered image;

determine respective irradiation parameters of the anatomical structures of the region of interest of the subject based on the position of the virtual light source relative to the anatomical structures of the region of interest;

generate a second volume-rendered image by removing one or more anatomical structures, of the anatomical structures, from the first volume-rendered image based on the respective irradiation parameters of the anatomical structures; and simultaneously display the first volume-rendered image and the second volume-rendered image.

2. The system of claim 1, wherein the one or more processors are further configured to:

determine whether the respective irradiation parameters satisfy respective irradiation parameter thresholds; and selectively remove the anatomical structures in the second volume-rendered image based on determining whether the respective irradiation parameters satisfy respective irradiation parameter thresholds.

3. The system of claim 1, wherein the respective irradiation parameters include irradiance or radiance.

4. The system of claim 1, wherein the one or more processors are further configured to:

determine whether the position of the virtual light source relative to the anatomical structures of the region of interest of the subject in the first volume-rendered image is adjusted; and selectively update the second volume-rendered image based on determining whether the position of the virtual light source relative to the anatomical structures of the region of interest of the subject in the first volume-rendered image is adjusted.

5. The system of claim 1, wherein the one or more processors are further configured to:

display a user interface element corresponding to the virtual light source in the first volume-rendered image.

6. The system of claim 1, wherein the one or more processors are further configured to:

entirely remove the one or more anatomical structures from the first volume-rendered image.

7. The system of claim 1, wherein the one or more processors are further configured to:

partially remove the one or more anatomical structures from the first volume-rendered image by adjusting respective opacity values of the one or more anatomical structures.

8. A method comprising:

receiving three-dimensional (3D) medical imaging data of a region of interest of a subject;

generating a first volume-rendered image of anatomical structures of the region of interest of the subject;

displaying the first volume-rendered image of the anatomical structures of the region of interest of the subject;

receiving a user input that selects a position of a virtual light source relative to the anatomical structures of the region of interest of the subject in the first volume-rendered image;

determining respective irradiation parameters of the anatomical structures of the region of interest of the subject based on the position of the virtual light source relative to the anatomical structures of the region of interest;

generating a second volume-rendered image by removing one or more anatomical structures, of the anatomical structures, from the first volume-rendered image based on the respective irradiation parameters of the anatomical structures; and simultaneously displaying the first volume-rendered image and the second volume-rendered image.

9. The method of claim 8, further comprising:

determining whether the respective irradiation parameters satisfy respective irradiation parameter thresholds; and selectively removing the anatomical structures in the second volume-rendered image based on determining whether the respective irradiation parameters satisfy respective irradiation parameter thresholds.

10. The method of claim 8, wherein the respective irradiation parameters include irradiance or radiance.

11. The method of claim 8, further comprising:

determining whether the position of the virtual light source relative to the anatomical structures of the region of interest of the subject in the first volume-rendered image is adjusted; and selectively updating the second volume-rendered image based on determining whether the position of the virtual light source relative to the anatomical structures of the region of interest of the subject in the first volume-rendered image is adjusted.

12. The method of claim 8, further comprising:

displaying a user interface element corresponding to the virtual light source in the first volume-rendered image.

13. The method of claim 8, further comprising:

entirely removing the one or more anatomical structures from the first volume-rendered image.

14. The method of claim 8, further comprising:

partially removing the one or more anatomical structures from the first volume-rendered image by adjusting respective opacity values of the one or more anatomical structures.

15. A non-transitory computer-readable medium storing instructions that, when executed by one or more processors, cause the one or more processors to:

receive three-dimensional (3D) medical imaging data of a region of interest of a subject;

generate a first volume-rendered image of anatomical structures of the region of interest of the subject;

display the first volume-rendered image of the anatomical structures of the region of interest of the subject;

receive a user input that selects a position of a virtual light source relative to the anatomical structures of the region of interest of the subject in the first volume-rendered image;

determine respective irradiation parameters of the anatomical structures of the region of interest of the subject based on the position of the virtual light source relative to the anatomical structures of the region of interest;

generate a second volume-rendered image by removing one or more anatomical structures, of the anatomical structures, from the first volume-rendered image based on the respective irradiation parameters of the anatomical structures; and simultaneously display the first volume-rendered image and the second volume-rendered image.

16. The non-transitory computer-readable medium of claim 15, wherein the instructions further cause the one or more processors to:

determine whether the respective irradiation parameters satisfy respective irradiation parameter thresholds; and selectively remove the anatomical structures in the second volume-rendered image based on determining whether the respective irradiation parameters satisfy respective irradiation parameter thresholds.

17. The non-transitory computer-readable medium of claim 15, wherein the respective irradiation parameters include irradiance or radiance.

18. The non-transitory computer-readable medium of claim 15, wherein the instructions further cause the one or more processors to:

determine whether the position of the virtual light source relative to the anatomical structures of the region of interest of the subject in the first volume-rendered image is adjusted; and selectively update the second volume-rendered image based on determining whether the position of the virtual light source relative to the anatomical structures of the region of interest of the subject in the first volume-rendered image is adjusted.

19. The non-transitory computer-readable medium of claim 15, wherein the instructions further cause the one or more processors to:

display a user interface element corresponding to the virtual light source in the first volume-rendered image.

20. The non-transitory computer-readable medium of claim 15, wherein the instructions further cause the one or more processors to:

entirely remove the one or more anatomical structures from the first volume-rendered image, or partially remove the one or more anatomical structures from the first volume-rendered image by adjusting respective opacity values of the one or more anatomical structures.

* * * * *